(12) United States Patent
Lynch et al.

(10) Patent No.: US 12,385,005 B2
(45) Date of Patent: Aug. 12, 2025

(54) COMPOSITIONS AND METHODS FOR IMPROVED MALONYL-CoA BIOSYNTHESIS USING 2-STAGE DYNAMIC METABOLIC CONTROL

(71) Applicant: Duke University, Durham, NC (US)

(72) Inventors: Michael Lynch, Durham, NC (US); Jeovanna Rios, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 18/187,102

(22) Filed: Mar. 21, 2023

(65) Prior Publication Data
US 2024/0132833 A1 Apr. 25, 2024
US 2024/0228945 A9 Jul. 11, 2024

Related U.S. Application Data

(60) Provisional application No. 63/269,646, filed on Mar. 21, 2022.

(51) Int. Cl.
| | |
|---|---|
| *C12N 1/20* | (2006.01) |
| *C07K 14/245* | (2006.01) |
| *C12N 9/88* | (2006.01) |
| *C12N 15/113* | (2010.01) |
| *C12N 15/52* | (2006.01) |
| *C12N 15/70* | (2006.01) |
| *C12P 7/46* | (2006.01) |
| *C12R 1/19* | (2006.01) |

(52) U.S. Cl.
CPC ............... *C12N 1/205* (2021.05); *C12N 9/88* (2013.01); *C12N 15/113* (2013.01); *C12N 15/52* (2013.01); *C12R 2001/19* (2021.05); *C12Y 401/01009* (2013.01)

(58) Field of Classification Search
None
See application file for complete search history.

(56) References Cited

U.S. PATENT DOCUMENTS

| | | | |
|---|---|---|---|
| 10,662,426 B2 | 5/2020 | Lynch et al. | |
| 11,236,370 B2 * | 2/2022 | Lynch | C12N 15/746 |
| 2011/0111458 A1 * | 5/2011 | Masuda | C12P 13/04 |
| | | | 435/252.33 |
| 2011/0125118 A1 | 5/2011 | Lynch | |
| 2017/0121707 A1 | 5/2017 | Lynch | |
| 2020/0248211 A1 * | 8/2020 | Lynch | C12N 9/0016 |

OTHER PUBLICATIONS

Forchhammer et al. (Heterotrimerization of PII-like signalling proteins: implications for PII-mediated signal transduction systems, Molecular Microbiology (1999) 33(2), 338-349) (Year: 1999).*

Liu, C. et al. Malonyl-CoA pathway: a promising route for 3-hydroxypropionate biosynthesis. Crit. Rev. Biotechnol. 37, 933-941 (2017).
Andreessen, B., et al. Poly(3-hydroxypropionate): a promising alternative to fossil fuel-based materials. Appl. Environ. Microbiol. 80, 6574-6582 (2014).
Li, S., et al., The Development of 2-stage Microfermentation Protocols for High Throughput Cell Factory Evaluations. bioRxiv 2022.02.25.481916 (2022) doi: 10.1101/2022.02.25.481916.
Milke, L., et al., Engineering intracellular malonyl-CoA availability in microbial hosts and its impact on polyketide and fatty acid synthesis. Appl. Microbiol. Biotechnol. 104, 6057-6065 (2020).
Milke, L., et al., Tailoring Corynebacterium glutamicum towards increased malonyl-CoA availability for efficient synthesis of the plant pentaketide noreugenin. Microb. Cell Fact. 18, 71 (2019).
Wink, M. Annual Plant Reviews, Functions and Biotechnology of Plant Secondary Metabolites. (John Wiley & Sons, 2010).
Robertsen, H. L., et al., Actinomycete-Derived Polyketides as a Source of Antibiotics and Lead Structures for the Development of New Antimicrobial Drugs. Antibiotics (Basel) 8, (2019).
Tokuyama, K et al. Magnesium starvation improves production of malonyl-CoA-derived metabolites in *Escherichia coli*. Metab. Eng. 52, 215-223 (2019).
Xu, P., et al., Genome-scale metabolic network modeling results in minimal interventions that cooperatively force carbon flux towards malonyl-CoA. Metab. Eng. 13, 578-587 (2011).
Xu, P., et al., Improving fatty acids production by engineering dynamic pathway regulation and metabolic control. https://www.pnas.org/doi/epdf/10.1073/pnas.1406401111 doi:10.1073/pnas.1406401111, last accessed Jun. 14, 2023.
Zhou, S. et al. Development of a growth coupled and multi-layered dynamic regulation network balancing malonyl-CoA node to enhance (2S)-naringenin biosynthesis in *Escherichia coli*. Metab. Eng. 67, 41-52 (2021).
Bhan, N., et al., Redirecting carbon flux into malonyl-CoA to improve resveratrol titers: Proof of concept for genetic interventions predicted by OptForce computational framework. Chem. Eng. Sci. 103, 109-114 (2013).
Sharan, S. K., et al., Recombineering: a homologous recombination-based method of genetic engineering. Nat. Protoc. 4, 206-223 (2009).
Sun, T., et al., Re-direction of carbon flux to key precursor malonyl-CoA via artificial small RNAs in photosynthetic *Synechocystis* sp. PCC 6803. Biotechnol. Biofuels 11, 26 (2018).
Shi, S., et al., Improving production of malonyl coenzyme A-derived metabolites by abolishing Snf1-dependent regulation of Acc1. MBio 5, e01130-14 (2014).
Li, S. J., et al., Growth rate regulation of *Escherichia coli* acetyl coenzyme A carboxylase, which catalyzes the first committed step of lipid biosynthesis. J. Bacteriol. 175, 332-340 (1993).

(Continued)

*Primary Examiner* — Manjunath N Rao
*Assistant Examiner* — Jae W Lee
(74) *Attorney, Agent, or Firm* — Benesch Friedlander Coplan & Aronoff LLP

(57) ABSTRACT

Methods and microorganisms for improved malonyl-CoA flux and production of products having malonyl-CoA as a precursor. The methods comprise dynamically regulating, in a stationary phase of a method, a nitrogen regulatory protein. The methods may dynamically regulate more than one gene.

9 Claims, 7 Drawing Sheets

(56) References Cited

OTHER PUBLICATIONS

Nomura, G., et al., Measurement of Intracellular Acetyl-CoA and Malonyl-CoA in Bacteria and Yeasts Using Acyl-CoA Cycling. Agric. Biol. Chem. 52, 843-844 (1988).
Johnson, A. O. et al., Design and application of genetically-encoded malonyl-CoA biosensors for metabolic engineering of microbial cell factories. Metab. Eng. 44, 253-264 (2017).
Fowler, Z. L., et al., Increased malonyl coenzyme A biosynthesis by tuning the *Escherichia coli* metabolic network and its application to flavanone production. Appl. Environ. Microbiol. 75, 5831-5839 (2009).
Krivoruchko, A., et al., Microbial acetyl-CoA metabolism and metabolic engineering. Metab. Eng. 28, 28-42 (2015).
Atsumi, S. et al., Directed evolution of Methanococcus jannaschii citramalate synthase for biosynthesis of 1-propanol and 1-butanol by *Escherichia coli*. Appl. Environ. Microbiol. 74, 7802-7808 (2008).
Lynch, M. D. Into new territory: improved microbial synthesis through engineering of the essential metabolic network. Curr. Opin. Biotechnol. 38, 106-111 (2016).
Li, S. et al., Dynamic control over feedback regulatory mechanisms improves NADPH flux and xylitol biosynthesis in engineered *E. coli*. Metab. Eng. 64, 26-40 (2021).
Ye, Z. et al., Two-stage dynamic deregulation of metabolism improves process robustness & scalability in engineered *E. coli*. Metab. Eng. 68, 106-118 (2021).
Heath, et al., Regulation of Malonyl-CoA Metabolism by Acyl-Acyl Carrier Protein and β-Ketoacyl-Acyl Carrier Protein Synthases in *Escherichia coli*. J. Biol. Chem. 270, 15531-15538 (1995).
Davis, M. S., et al., Overproduction of acetyl-CoA carboxylase activity increases the rate of fatty acid biosynthesis in *Escherichia coli*. J. Biol. Chem. 275, 28593-28598 (2000).

Subrahmanyam, S. Fatty acid and biotin metabolism in *Escherichia coli*. (University of Illinois at Urbana- Champaign, 1998).
Hauf, W., et al., Interaction of the Nitrogen Regulatory Protein GlnB (PII) with Biotin Carboxyl Carrier Protein (BCCP) Controls Acetyl-CoA Levels in the Cyanobacterium *Synechocystis* sp. PCC 6803. Front. Microbiol. 7, 1700 (2016).
Li, S., et al., Dynamic control over feedback regulation identifies pyruvate-ferredoxin oxidoreductase as a central metabolic enzyme in stationary phase *E. coli*. Cold Spring Harbor Laboratory 2020. 07.26.219949 (2020) doi:10.1101/2020.07.26.219949.
Ye, Z. et al., *Escherichia coli* Cas1/2 Endonuclease Complex Modifies Self-Targeting CRISPR/Cascade Spacers Reducing Silencing Guide Stability. ACS Synth. Biol. (2020) doi: 10.1021/acssynbio.0c00398.
Yang, D., et al. Repurposing type III polyketide synthase as a malonyl-CoA biosensor for metabolic engineering in bacteria. Proc. Natl. Acad. Sci. U. S. A. 115, 9835-9844 (2018).
Cortés, J. et al., Identification and cloning of a type III polyketide synthase required for diffusible pigment biosynthesis in Saccharopolyspora erythraea. Mol. Microbiol. 44, 1213-1224 (2002).
Menacho-Melgar, R. et al. Scalable, two-stage, autoinduction of recombinant protein expression in *E. coli* utilizing phosphate depletion. Biotechnol. Bioeng. 26, 44 (2020).
Moreb, E. A. et al., Media Robustness and Scalability of Phosphate Regulated Promoters Useful for Two-Stage Autoinduction in *E. coli*. ACS Synth. Biol. 9, 1483-1486 (2020).
Kumar et al., "Metabolic regulation of *Escherichia coli* and its gdhA, glnL, gltB, D mutants under different carbon and nitrogen limitations in the continuous culture", Microbial Cell Factories, Jan. 27, 2010, vol. 9, article 8, pp. 1-17.
International Search Report and Written Opinion issued in PCT application No. PCT/US23/64738, mailing date Sep. 5, 2023.

\* cited by examiner

| Plasmids | | | | | | |
|---|---|---|---|---|---|---|
| Name | Insert | Promoter | Origin | Resistance | Addgene | Source |
| pSMART-HC-Kan | -- | -- | colE1 | Kan | -- | Lucigen |
| pHCKan-rppA | rppA | yibDp [35] | colE1 | Kan | | This study |
| pCASCADE-ev | -- | ugpBp Moreb, et al ACS Synth Biol (2020) | p15a | Cm | 65821 | Ye, et al ACS Synth Biol (2020) |
| pCASCADE-g2 | gltAp2 gRNA | ugpBp Moreb, et al ACS Synth Biol (2020) | p15a | Cm | 65817 | Ye, et al ACS Synth Biol (2020) |
| pCASCADE-z | zwfp gRNA | ugpBp Moreb, et al ACS Synth Biol (2020) | p15a | Cm | 65825 | Ye, et al ACS Synth Biol (2020) |
| pCASCADE-g2z | gltAp2, zwfp gRNA array | ugpBp Moreb, et al ACS Synth Biol (2020) | p15a | Cm | 71338 | Ye, et al ACS Synth Biol (2020) |
| pCASCADE-fg2z | fabIp, gltAp2, zwfp gRNA array | ugpBp Moreb, et al ACS Synth Biol (2020) | p15a | Cm | | This study |

FIG 2

| Name | Insert | Promoter | Origin | Resistance | Addgene | Source |
|---|---|---|---|---|---|---|
| pCASCADE-b1 | glnBp2 gRNA | ugpBp Moreb, et al ACS Synth Biol (2020) | p15a | Cm | 162391 | Ye, et al ACS Synth Biol (2020) |
| pCASCADE-b2 | glnBp2 gRNA | ugpBp Moreb, et al ACS Synth Biol (2020) | p15a | Cm | 162391 | Ye, et al ACS Synth Biol (2020) |
| pCASCADE-b1b2 | glnBp2 gRNA | ugpBp Moreb, et al ACS Synth Biol (2020) | p15a | Cm | 162391 | Ye, et al ACS Synth Biol (2020) |
| pCASCADE-g2zb2 | gltAp2, zwfp, gRNA array | ugpBp Moreb, et al ACS Synth Biol (2020) | p15a | Cm | | This study |
| pCASCADE-fg2zb2 | fablp, gltAp2, zwfp, glnBp2 gRNA array | ugpBp Moreb, et al ACS Synth Biol (2020) | p15a | Cm | | This study |

FIG 2 continued

| Strains | | |
|---|---|---|
| DLF_S0025 | F-, λ-, Δ(araD-araB)567, lacZ4787(del)(::rrnB-3), rph-1, Δ(rhaD-rhaB)568, hsdR514, ΔackA-pta, ΔpoxB, ΔpflB, ΔldhA, ΔadhE, ΔiclR, ΔarcA, ΔsspB, Δcas3::tm-ugpb-sspB-yibDp-casA | Ye, et al ACS Synth Biol (2020) |
| DLF_S0043 | DLF_S0025, gltA-DAS+4-zeoR | Li et al, *Cold Spring Harbor Laoratory* 2020 |
| DLFS_0044 | DLF_S0025, gltA-DAS+4-zeoR, zwf-DAS+4-bsdR | Li et al, *Cold Spring Harbor Laoratory* 2020 |
| DLF_SJR001 | DLF_S0025, fabI-DAS+4-gentR | This study |
| DLF_SJR001 | DLF_S0025, fabI-sfGFP-gentR | This study |
| DLF_SJR003 | DLF_S0025, fabI-sfGFP-DAS+4-gentR | This study |
| DLF_SJR004 | DLF_S0025, glnB-DAS+4-apmR | This study |
| DLF_SJR005 | DLF_S0025, glnB-sfGFP-apmR | This study |
| DLF_SJR006 | DLF_S0025, glnB-sfGFP-DAS+4-apmR | This study |
| DLF_SJR007 | DLF_S0025, gltA-DAS+4-zeoR, zwf-DAS+4-bsdR | Li et al, *Cold Spring Harbor Laoratory* 2020 |

FIG 3

| Strains, continued | | |
|---|---|---|
| DLF_SJR008 | DLF_S0025, fabI-DAS+4-gentR, gltA-DAS+4-zeoR, zwf-DAS+4-bsdR | This study |
| DLF_SJR009 | DLF_S0025, gltA-DAS+4-zeoR, zwf-DAS+4-bsdR, glnB-DAS+4-ampR | This study |
| DLF_SJR010 | DLF_S0025, fabI-DAS+4-gentR, gltA-DAS+4-zeoR, zwf-DAS+4-bsdR, glnB-DAS+4-ampR | This study |

FIG 3, continued

COMPOSITIONS AND METHODS FOR IMPROVED MALONYL-CoA BIOSYNTHESIS USING 2-STAGE DYNAMIC METABOLIC CONTROL

PRIORITY CLAIM

This application claims the benefit of U.S. Provisional Application No. 63/269,646 filed Mar. 21, 2022, which application is incorporated herein by reference in its entirety.

STATEMENT AS TO FEDERALLY SPONSORED RESEARCH

The invention was made with Government support under Federal Grant HR0011-14-C-0075 awarded by DARPA, Grant #N00014-16-1-2558 awarded by ONR, and Grant #4000181535 awarded by SERDP. The Federal Government has certain rights to this invention.

BACKGROUND

Malonyl-CoA is a central metabolite and intermediate that serves as a precursor for a wide range of products such as biofuels/biopolymers, plant natural products, polyketides and pharmaceutical intermediates. Efforts to improve flux to malonyl-CoA have been extensive and have included nutrient starvation, dynamic control, and gene manipulation including additions and deletions in *E. coli* as well as other microbial hosts.

In *E. coli*, malonyl-CoA is a tightly regulated metabolite, responsible for fatty acid biosynthesis, and as such its biosynthesis is coordinated with the rate of fatty acid biosynthesis, phospholipid production, and cellular growth. Under normal metabolic conditions, only a small portion of the acetyl-CoA pool is converted to malonyl-CoA by action of acetyl-CoA carboxylase (ACCase). Malonyl-CoA flux and pools are regulated with nested feedback loops and connection to cell-wide energy and carbon conditions, to a degree that is greater than most other metabolic branch points and committed steps, and in natural organisms its intracellular concentrations are kept in the low to mid micromolar range, some 10 to 100-fold less than acetyl-CoA during aerobic growth. The metabolites scarcity and complicated regulatory connections are widely accepted to have impeded development of bioprocesses for these products. Unraveling central metabolites from the host network is a central part of platform strain development.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

In some aspects, in invention comprises a genetically modified microorganism having a synthetic metabolic valve for dynamic and selective regulation of a nitrogen regulatory protein (glnB). The synthetic metabolic valve may include gene expression-silencing of a glnB gene, selective enzymatic degradation of a glnB protein, or any combination of the two. When the synthetic metabolic valve is selectively activated to silence a glnB gene and/or degrade a glnB protein in response to change in the growth media in which the genetically modified microorganism is growing.

In some aspects, the genetically modified microorganism has additional synthetic metabolic valves are directed to silencing a gene that is: enoyl-ACP reductase (fabI), citrate synthase (gltA), glucose-6-phosphate-1-dehydrogenase (zwf), or any combinations of these or the additional synthetic metabolic valves are directed to selective enzymatic degradation of a protein that is: enoyl-ACP reductase (fabI), citrate synthase (gltA), glucose-6-phosphate-1-dehydrogenase (zwf), or any combinations of these.

In some aspects, the invention fully describes a bioprocess for production of a product from a genetically modified microorganism comprising a synthetic metabolic valve directed to dynamic and selective regulation of a nitrogen regulatory protein (glnB).

Other methods, features and/or advantages is, or will become, apparent upon examination of the following figures and detailed description. It is intended that all such additional methods, features, and advantages be included within this description and are protected by the accompanying claims.

BRIEF DESCRIPTION OF DRAWINGS

The novel features of the invention are set forth with particularity in the claims. A better understanding of the features and advantages of the present invention will be obtained by reference to the following detailed description that sets forth illustrative aspects, in which the principles of the invention are used, and the accompanying drawings of which:

FIG. 2 is a table of plasmids for practice of an aspect of this invention.

FIG. 3 is a table of microorganism strains for practice of an aspect of this invention.

DETAILED DESCRIPTION

Figure 1A:
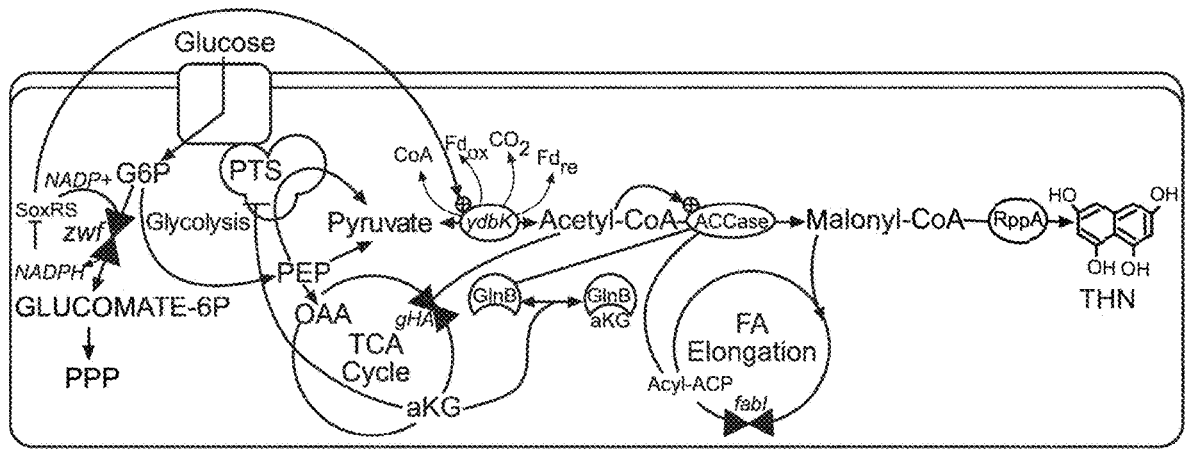
FIG. 1A-1D: 1A) Schematic depicting dynamic control over GltA, Zwf, FabI, and GlnB levels improves THN production. Red double triangle "valves" indicate central metabolic proteins targeted for dynamic reduction. Reduced GltA activity reduces aKG pools and alleviates aKG mediated inhibition of PTS-dependent glucose uptake (specifically, PtsI), improving glucose uptake rates, glycolytic fluxes and pyruvate production. Reduced Zwf activity reduces NADPH levels thereby activating the SoxRS regulon and increases activity of the pyruvate-ferredoxin oxidoreductase (Pfo, ydbK) improving acetyl-CoA fluxes. Reduced FabI activity dynamically reduces acyl-ACP pools to alleviate inhibition of ACCase. Reduced GlnB levels reduces GlnB mediated inhibition of ACCse (in the absence of alpha-Ketoglutarate). 1B) An overview of two stage dynamic metabolic control. Biomass is grown to a stationary phase where depletion of a limiting nutrient (i.e. phosphate) turns "off" competing pathways, while turning "on" desired production route. (1C-1D) Genetic circuitry underlying two stage dynamic control of protein levels after phosphate depletion during the stationary phase. 1C) (i) Engineered strains express an array of silencing gRNAs from the low phosphate inducible ugpB gene promoter. (ii) Engineered strains also express native nuclease deficient *E. coli* Cascade complex capable of gene silencing, which leads to (iii) targeted gene silencing upon phosphate depletion. 1D) Inducible proteolysis. (i)C-terminal DAS+4 degron tags that once translated allows for controlled proteolysis. (ii) SspB chaperone expression is under control of a low phosphate inducible promoter, which enables (iii) chaperone assisted proteolysis via the ClpXP protease under low phosphate conditions.
Figure 1B:
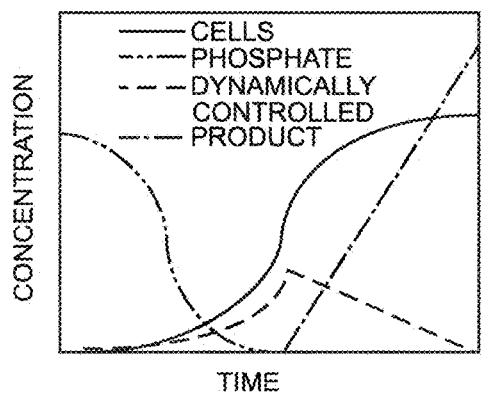
Figure 1C:
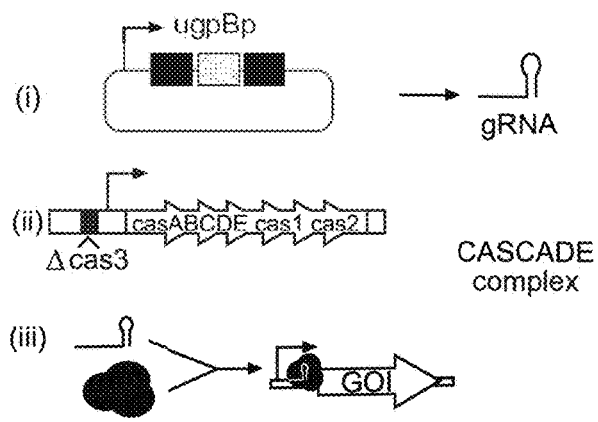
Figure 1D:
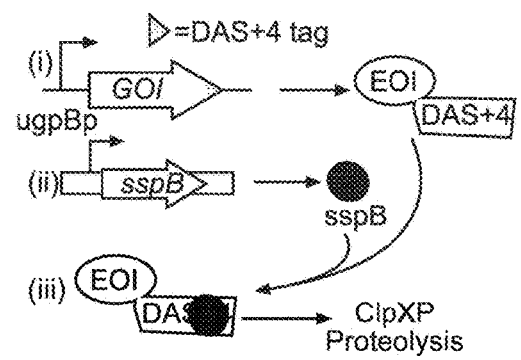
Figure 4A:
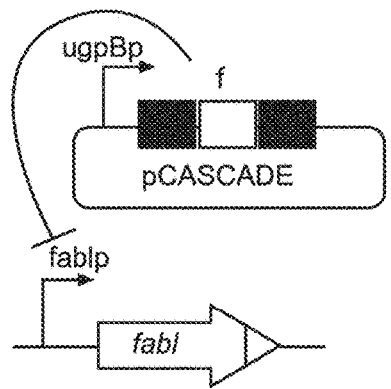
FIG. 4A-4D: 4A-4B) engineered strains express an array of silencing gRNAs from the low phosphate inducible ugpB gene promotor. 4C-4D) genes were tagged with a C-terminal sfGFP (+/−a DAS+4 tag) and protein levels quantified via an ELISA. All data were taken 24 h post induction by phosphate depletion in microfermentations.
Figure 4B:
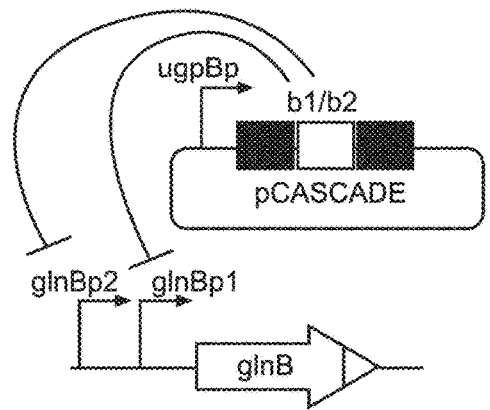
Figure 4C:
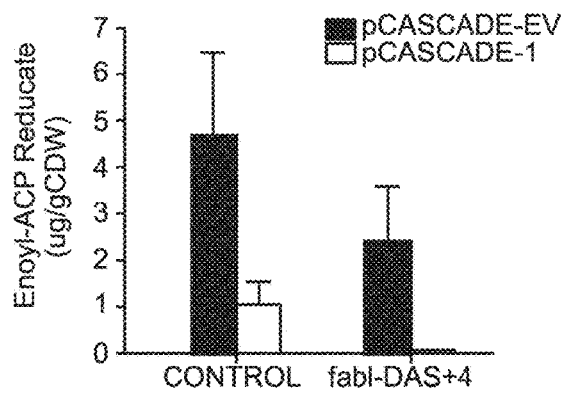
Figure 4D:
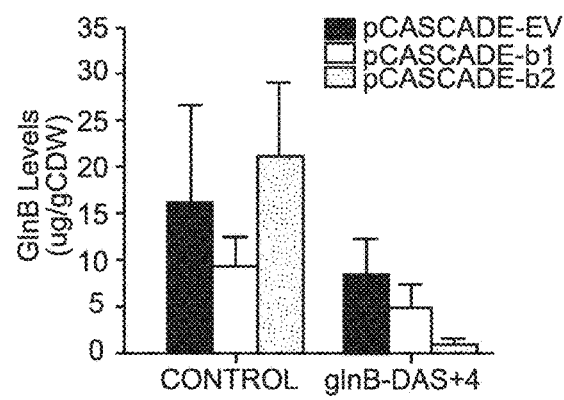

Malonyl-CoA is a platform chemical that serves as a precursor for a wide range of high value chemicals. In *E. coli*, malonyl-CoA levels and flux are tightly regulated. We demonstrate the use of two-stage dynamic metabolic control to improve malonyl-CoA biosynthesis in engineered *E. coli*. We have previously demonstrated the use of two-stage dynamic metabolic control to improve stationary phase glucose uptake, central metabolism and product biosynthesis. In this work, we demonstrate that the coordinated dynamic reductions in the levels of fabI (enoyl-ACP reductase), gltA (citrate synthase), zwf (glucose-6-phosphate dehydrogenase) and glnB (nitrogen regulatory protein PII-1) during stationary phase lead to synergistic improvements in malonyl-CoA flux and product biosynthesis. Importantly, the largest improvements in flux require all four metabolic valves and the coordinated deregulation of 1) glucose uptake, 2) acetyl-CoA production and 3) acetyl-CoA carboxylase activity, which is directly regulated by nitrogen regulatory protein and allosterically regulated by acyl-ACPs which are produced by enoyl-ACP reductase. This approach is broadly applicable for the production of malonyl-CoA dependent products.

Referring now to FIG. 1, two-stage dynamic metabolic control offers a potential route to successfully deregulate metabolism and unravel central metabolites from the host regulatory network. During a non-growing stationary phase, levels of central metabolic and regulatory proteins can be pushed beyond the boundary conditions imposed by growing cells, leading to more optimal deregulated production states. We have previously demonstrated the use of two-stage dynamic metabolic control in *E. coli* to deregulate central metabolism and improve product biosynthesis, as well as process robustness and scalability.

Specifically, we have reported the use of a combination of controlled proteolysis and CRISPR based gene silencing to reduce levels of key metabolic enzymes including citrate synthase (gltA, "G"-valve), glucose-6-phosphae dehydrogenase (zwf, "Z"-valve) and enoyl-ACP reductase (fabI "F"-valve), which has led to improvements in the stationary phase biosynthesis of pyruvic acid, alanine, citramalate and xylitol.

As illustrated in FIG. 1, dynamic reduction of citrate synthase ("G") levels leads to reduced levels of alpha-ketoglutarate, an inhibitor of PTS-dependent glucose uptake. Therefore, its reduction deregulates PTS-dependent sugar uptake which enhances stationary phase metabolism via improved pyruvate production and glycolytic fluxes. Dynamic reduction of glucose 6-phosphate dehydrogenase ("Z") has been shown to reduce NADPH levels, which in turn activates the SoxRS regulon. When SoxRS regulon is activated, it increases the oxidation of pyruvate to acetyl-CoA. The combination of both "G" and "Z" valves has led to large increases in the biosynthesis of citramalate, which is produced from pyruvate and acetyl-CoA. Dynamic reduction in enoyl-ACP reductase ("F") levels has been shown to dynamically reduce acyl-ACP pools which have several regulatory roles. Firstly, reduced acyl-ACP/CoA pools alleviate inhibition of them membrane bound transhydrogenase (PntAB) improving NADPH fluxes and stationary phase xylitol biosynthesis. Perhaps more importantly, enoyl-ACP reduced acyl-ACP pools alleviate inhibition of acetyl-coA carboxylase. 2-stage dynamic reduction of enoyl-ACP activity using a temperature sensitive fabI allele, has been used to improve the biosynthesis of 3-hydroxy-propionic acid in *E. coli*.

In order to improve malonyl-CoA biosynthesis, we leveraged the "G", "Z" and "F" valves along with dynamic reductions in GlnB levels or a "B" valve. GlnB encodes for a nitrogen regulator protein (P-II) which has been shown to inhibit ACCase in an alpha-ketoglutarate dependent manner (FIG. 1). This level of regulation has likely evolved to coordinate fatty acid biosynthesis with nitrogen availability and amino acid (glutamate) biosynthesis. Unfortunately, alpha-ketoglutarate levels have competing regulatory effects, reduced alpha-ketoglutarate levels (resulting from the "G" valve) alleviated inhibition of glucose uptake improving stationary phase biosynthesis but also lead to increased GlnB based inhibition of ACCase, presenting a block in malonyl-CoA synthesis. We hypothesized that dynamic reductions in GlnB levels would improve malonyl-CoA production in strains with "G" valves. This work demonstrates the synergistic effects of "G", "Z", "F", in combination with the "B" valve on the flux through malonyl-CoA.

I. Definitions

Unless otherwise defined, all technical and scientific terms used herein have the same meaning as commonly understood by one of ordinary skill in the art to which this invention pertains. In case of conflict, the present specification, including definitions, will control.

Unless otherwise specified, "a," "an," "the," "one or more of," and "at least one" are used interchangeably. The singular forms "a", "an," and "the" are inclusive of their plural forms.

The recitations of numerical ranges by endpoints include all numbers subsumed within that range (e.g., 0.5 to 5 includes 1, 1.5, 2, 2.75, 3, 3.80, 4, 5, etc.).

The term "about," when referring to a value or to an amount of mass, weight, time, volume, concentration, or percentage is meant to encompass variations of +10% from the specified amount. The terms "comprising" and "including" are intended to be equivalent and open-ended. The phrase "consisting essentially of" means that the composition or method may include additional ingredients and/or steps, but only if the additional ingredients and/or steps do not materially alter the basic and novel characteristics of the claimed composition or method. The phrase "selected from the group consisting of" is meant to include mixtures of the listed group.

Moreover, the present disclosure also contemplates that in some aspects, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

The term "heterologous DNA," "heterologous nucleic acid sequence," and the like as used herein refers to a nucleic acid sequence wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid, such as a nonnative promoter driving gene expression. The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome). As used herein, chromosomal and native and endogenous refer to genetic material of the host microorganism.

As used herein, the term "gene disruption," or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

Bio-production, Micro-fermentation (microfermentation) or Fermentation, as used herein, may be aerobic, microaerobic, or anaerobic.

When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

Species and other phylogenic identifications are according to the classification known to a person skilled in the art of microbiology.

Enzymes are listed here within, with reference to a UniProt identification number, which would be well known to one skilled in the art. The UniProt database can be accessed at www.UniProt.org. When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

The meaning of abbreviations is as follows: "C" means Celsius or degrees Celsius, as is clear from its usage, DCW means dry cell weight, "s" means second(s), "min" means minute(s), "h," "hr," or "hrs" means hour(s), "psi" means pounds per square inch, "nm" means nanometers, "d" means day(s), "μL" or "uL" or "ul" means microliter(s), "mL" means milliliter(s), "L" means liter(s), "mm" means millimeter(s), "nm" means nanometers, "mM" means millimolar, "μM" or "uM" means micromolar, "M" means molar, "mmol" means millimole(s), "μmol" or "uMol" means micromole(s)", "g" means gram(s), "μg" or "ug" means microgram(s) and "ng" means nanogram(s), "PCR" means polymerase chain reaction, "OD" means optical density, "OD600" means the optical density measured at a photon wavelength of 600 nm, "kDa" means kilodaltons, "g" means the gravitation constant, "bp" means base pair(s), "kbp" means kilobase pair(s), "% w/v" means weight/volume percent, "% v/v" means volume/volume percent, "IPTG" means isopropyl-u-D-thiogalactopyranoiside, "aTc" means anhydrotetracycline, "RBS" means ribosome binding site, "rpm" means revolutions per minute, "HPLC" means high performance liquid chromatography, and "GC" means gas chromatography.

Overview of Invention Aspects

In some aspects, in invention comprises a genetically modified microorganism having a synthetic metabolic valve for dynamic and selective regulation of a nitrogen regulatory protein (glnB). The synthetic metabolic valve may include gene expression-silencing of a glnB gene, selective enzymatic degradation of a glnB protein, or any combination of the two. When the synthetic metabolic valve is selectively activated to silence a glnB gene and/or degrade a glnB protein in response to change in the growth media in which the genetically modified microorganism is growing.

In some aspects, the genetically modified microorganism may also include additional synthetic metabolic valve(s) directed to a silencing gene expression of one or more genes other than glnB gene; or a selective enzymatic degradation synthetic metabolic valve inducing selective enzymatic degradation of one or more proteins other than the glnB protein, or any combination of the two.

In some aspects, the genetically modified microorganism has additional synthetic metabolic valves are directed to silencing a gene that is: enoyl-ACP reductase (fabI), citrate synthase (gltA), glucose-6-phosphate-1-dehydrogenase (zwf), or any combinations of these or the additional synthetic metabolic valves are directed to selective enzymatic degradation of a protein that is: enoyl-ACP reductase (fabI), citrate synthase (gltA), glucose-6-phosphate-1-dehydrogenase (zwf), or any combinations of these.

In some aspects, the genetically modified microorganism includes, in addition to the glnB synthetic metabolic valve, a second synthetic metabolic valve for dynamic and selective regulation of enoyl-ACP reductase (fabI), the synthetic metabolic valve comprising: gene expression-silencing of a fabI gene, selective enzymatic degradation of fabI protein, or a combination thereof; and a third synthetic metabolic valve for dynamic and selective regulation of glucose-6-phosphate-1-dehydrogenase (zwf), the synthetic metabolic valve comprising: gene expression-silencing of a zwf gene, selective enzymatic degradation of zwf protein, or a combination thereof; and a fourth synthetic metabolic valve for dynamic and selective regulation of citrate synthase (gltA), the synthetic metabolic valve comprising: gene expression-silencing of a gltA gene, selective enzymatic degradation of gltA protein, or a combination thereof.

In some aspects a change in the growth media is phosphate depletion from the growth media. In some aspects, the genetically modified microorganism o is an *E. coli* microorganism. In some aspects, the synthetic metabolic valve comprises: a gene encoding at least one small guide RNA specific for targeting more than one gene of an enzyme essential for growth of the genetically modified microorganism.

In some aspects, the invention fully describes a bioprocess for production of a product from a genetically modified microorganism, the bioprocess including a step of providing a genetically modified microorganism. This microorganism including: a production pathway for a product, the production pathway having malonyl-CoA as a biosynthetic precursor of the product; a synthetic metabolic valve for dynamic and selective regulation of a nitrogen regulatory protein (glnB), the synthetic metabolic valve comprising: gene expression-silencing of a glnB gene, selective enzymatic degradation of a glnB protein, or a combination thereof; and an additional synthetic metabolic valve(s) for dynamic and selective regulation of one or more genes in addition to the glnB gene; or a selective enzymatic degradation of one or more proteins in addition to the glnB protein. The method also includes steps of growing the genetically modified microorganism in a media; transitioning from microorganism growth to stationary productive phase, the transition comprising: reducing or stopping genetically modified microorganism growth at least partially by controlled depletion of a limiting nutrient from the media, activation of synthetic metabolic valves, increasing the available malonyl-CoA pool. The final step of the method would be producing a product in the stationary productive phase.

Disclosed Aspects Are Non-Limiting

While various aspects of the present invention have been shown and described herein, it is emphasized that such aspects are provided by way of example only. Numerous variations, changes and substitutions may be made without departing from the invention herein in its various aspects. Specifically, and for whatever reason, for any grouping of compounds, nucleic acid sequences, polypeptides including specific proteins including functional enzymes, metabolic pathway enzymes or intermediates, elements, or other compositions, or concentrations stated or otherwise presented herein in a list, table, or other grouping unless clearly stated otherwise, it is intended that each such grouping provides the basis for and serves to identify various subset aspects, the subset aspects in their broadest scope comprising every subset of such grouping by exclusion of one or more members (or subsets) of the respective stated grouping. Moreover, when any range is described herein, unless clearly stated otherwise, that range includes all values therein and all sub-ranges therein.

Also, and more generally, in accordance with disclosures, discussions, examples and aspects herein, there may be employed conventional molecular biology, cellular biology, microbiology, and recombinant DNA techniques within the skill of the art. Such techniques are explained fully in the literature. See, e.g., Sambrook and Russell, "Molecular Cloning: A Laboratory Manual," Third Edition 2001 (volumes 1-3), Cold Spring Harbor Laboratory Press, Cold Spring Harbor, N.Y.; Animal Cell Culture, R. I. Freshney, ed., 1986. These published resources are incorporated by reference herein.

The following published resources are incorporated by reference herein for description useful in conjunction with the invention described herein, for example, methods of industrial bio-production of chemical product(s) from sugar sources, and also industrial systems that may be used to achieve such conversion (Biochemical Engineering Fundamentals, 2nd Ed. J. E. Bailey and D. F. Ollis, McGraw Hill, New York, 1986, e.g.Chapter 9, pages 533-657 for biological reactor design; Unit Operations of Chemical Engineering, 5th Ed., W. L. McCabe et al., McGraw Hill, New York 1993, e.g., for process and separation technologies analyses; Equilibrium Staged Separations, P. C. Wankat, Prentice Hall, Englewood Cliffs, NJ USA, 1988, e.g., for separation technologies teachings).

All publications, patents, and patent applications mentioned in this specification are entirely incorporated by reference.

General Consideration

I. Carbon Sources

Bio-production media, which is used in the present invention with recombinant microorganisms must contain suitable carbon sources or substrates for both growth and production stages. Suitable substrates may include but are not limited a combination of glucose, sucrose, xylose, mannose, arabinose, oils, carbon dioxide, carbon monoxide, methane, methanol, formaldehyde, or glycerol. It is contemplated that all of the above-mentioned carbon substrates and mixtures thereof are suitable in the present invention as a carbon source(s).

II. Microorganisms

Features as described and claimed herein may be provided in a microorganism selected from the listing herein, or another suitable microorganism, that also comprises one or more natural, introduced, or enhanced product bio-production pathways. Thus, in some aspects the microorganism(s) comprise an endogenous product production pathway (which may, in some such aspects, be enhanced), whereas in other aspects the microorganism does not comprise an endogenous product production pathway.

More particularly, based on the various criteria described herein, suitable microbial hosts for the bio-production of a chemical product generally may include, but are not limited to the organisms described in the Methods Section.

The host microorganism or the source microorganism for any gene or protein described here may be selected from the following list of microorganisms: *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces,* and *Pseudomonas*. In some aspects the host microorganism is an *E. coli* microorganism.

III. Media and Culture Conditions

In addition to an appropriate carbon source, such as selected from one of the herein-disclosed types, bio-production media must contain suitable minerals, salts, cofactors, buffers and other components, known to those skilled in the art, suitable for the growth of the cultures and promotion of chemical product bio-production under the present invention.

Another aspect of the invention regards media and culture conditions that comprise genetically modified microorganisms of the invention and optionally supplements.

Typically cells are grown at a temperature in the range of about 25° C. to about 40° C. in an appropriate medium, as well as up to 70° C. for thermophilic microorganisms. Suitable growth media are well characterized and known in the art. Suitable pH ranges for the bio-production are between pH 2.0 to pH 10.0, where pH 6.0 to pH 8.0 is a typical pH range for the initial condition. However, the actual culture conditions for a particular aspect are not meant to be limited by these pH ranges. Bio-productions may be performed under aerobic, microaerobic or anaerobic conditions with or without agitation.

IV. Bio-production Reactors and Systems

Fermentation systems utilizing methods and/or compositions according to the invention are also within the scope of the invention. Any of the recombinant microorganisms as described and/or referred to herein may be introduced into an industrial bio-production system where the microorganisms convert a carbon source into a product in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to a selected chemical product. Bio-productions may be performed under aerobic, microaerobic, or anaerobic conditions, with or without agitation. Industrial bio-production systems and their operation are well-known to those skilled in the arts of chemical engineering and bioprocess engineering.

The amount of a product produced in a bio-production media generally can be determined using a number of methods known in the art, for example, high performance liquid chromatography (HPLC), gas chromatography (GC), or GC/Mass Spectroscopy (MS).

V. Genetic Modifications, Nucleotide Sequences, and Amino Acid Sequences

Aspects of the present invention may result from introduction of an expression vector into a host microorganism, wherein the expression vector contains a nucleic acid sequence coding for an enzyme that is, or is not, normally found in a host microorganism.

The ability to genetically modify a host cell is essential for the production of any genetically modified (recombinant) microorganism. The mode of gene transfer technology may be by electroporation, conjugation, transduction, or natural transformation. A broad range of host conjugative plasmids and drug resistance markers are available. The cloning vectors are tailored to the host organisms based on the nature of antibiotic resistance markers that can function in that host. Also, as disclosed herein, a genetically modified (recombinant) microorganism may comprise modifications other than via plasmid introduction, including modifications to its genomic DNA.

More generally, nucleic acid constructs can be prepared comprising an isolated polynucleotide encoding a polypeptide having enzyme activity operably linked to one or more (several) control sequences that direct the expression of the coding sequence in a microorganism, such as E. coli, under conditions compatible with the control sequences. The isolated polynucleotide may be manipulated to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well established in the art.

The control sequence may be an appropriate promoter sequence, a nucleotide sequence that is recognized by a host cell for expression of a polynucleotide encoding a polypeptide of the present invention. The promoter sequence may contain transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. The techniques for modifying and utilizing recombinant DNA promoter sequences are well established in the art.

For various aspects of the invention the genetic manipulations may include a manipulation directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected culture conditions. Genetic manipulation of nucleic acid sequences may increase copy number and/or comprise use of mutants of an enzyme related to product production. Specific methodologies and approaches to achieve such genetic modification are well known to one skilled in the art.

In various aspects, to function more efficiently, a microorganism may comprise one or more gene deletions. For example, in E. coli, the genes encoding the lactate dehydrogenase (ldhA), phosphate acetyltransferase (pta), pyruvate oxidase (poxB), pyruvate-formate lyase (pflB), methylglyoxal synthase (mgsA), acetate kinase (ackA), alcohol dehydrogenase (adhE), the clpXP protease specificity enhancing factor (sspB), the ATP-dependent Lon protease (lon), the outer membrane protease (ompT), the arcA transcriptional dual regulator (arcA), and the iclR transcriptional regulator (iclR) may be disrupted, including deleted. Such gene disruptions, including deletions, are not meant to be limiting, and may be implemented in various combinations in various aspects. Gene deletions may be accomplished by numerous strategies well known in the art, as are methods to incorporate foreign DNA into a host chromosome.

In various aspects, to function more efficiently, a microorganism may comprise one or more synthetic metabolic valves, composed of enzymes targeted for controlled proteolysis, expression silencing or a combination of both controlled proteolysis and expression silencing. For example, one enzyme encoded by one gene or a combination of numerous enzymes encoded by numerous genes in E. coli may be designed as synthetic metabolic valves to alter metabolism and improve product formation. Representative genes in E. coli may include but are not limited to the following: fabI, zwf, gltA, ppc, udhA, lpd, sucD, aceA, pfkA, lon, rpoS, pykA, pykF, tktA or tktB. It is appreciated that it is well known to one skilled in the art how to identify homologues of these genes and or other genes in additional microbial species.

For all nucleic acid and amino acid sequences provided herein, it is appreciated that conservatively modified variants of these sequences are included and are within the scope of the invention in its various aspects. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various aspects of the invention, as are methods and systems comprising such sequences and/or microorganisms.

Accordingly, as described in various sections above, some compositions, methods and systems of the present invention comprise providing a genetically modified microorganism that comprises both a production pathway to make a desired product from a central intermediate in combination with synthetic metabolic valves to redistribute flux.

Aspects of the invention also regard provision of multiple genetic modifications to improve microorganism overall effectiveness in converting a selected carbon source into a selected product. Particular combinations are shown, such as in the Examples, to increase specific productivity, volumetric productivity, titer and yield substantially over more basic combinations of genetic modifications.

In addition to the above-described genetic modifications, in various aspects genetic modifications, including synthetic metabolic valves also are provided to increase the pool and availability of the cofactor NADPH and/or NADH which may be consumed in the production of a product.

VI. Synthetic Metabolic Valves

Use of synthetic metabolic valves allows for simpler models of metabolic fluxes and physiological demands during a production phase, turning a growing cell into a stationary phase biocatalyst. These synthetic metabolic valves can be used to turn off essential genes and redirect carbon, electrons, and energy flux to product formation in a multi-stage fermentation process. One or more of the following provides the described synthetic valves: 1) transcriptional gene silencing or repression technologies in combination with 2) inducible and selective enzyme degradation and 3) nutrient limitation to induce a stationary or non-dividing cellular state. SMVs are generalizable to any pathway and microbial host. These synthetic metabolic valves allow for novel rapid metabolic engineering strategies useful for the production of renewable chemicals and fuels and any product that can be produced via whole cell catalysis.

In particular, the invention describes the construction of synthetic metabolic valves comprising one or more or a combination of the following: controlled gene silencing and controlled proteolysis. It is appreciated that one well skilled in the art is aware of several methodologies for gene silencing and controlled proteolysis.

VI.A Gene Silencing

In particular, the invention describes the use of controlled gene silencing to provide the control over metabolic fluxes in controlled multi-stage fermentation processes. There are several methodologies known in the art for controlled gene silencing, including but not limited to mRNA silencing or RNA interference, silencing via transcriptional repressors and CRISPR interference. Methodologies and mechanisms for RNA interference are taught by Agrawal et al. "RNA Interference: Biology, Mechanism, and Applications" Microbiology and Molecular Biology Reviews, December 2003; 67 (4) p657-685. DOI: 10.1128/MMBR.67.657-685.2003. Methodologies and mechanisms for CRISRPR interference are taught by Qi et al. "Repurposing CRISPR as an RNA-guided platform for sequence-specific control of gene expression" Cell February 2013; 152 (5) p1173-1183. DOI: 10.1016/j.cell.2013.02.022. In addition, methodologies, and mechanisms for CRISRPR interference using the native *E. coli* CASCADE system are taught by Luo et al. "Repurposing endogenous type I CRISPR-Cas systems for programmable gene repression" NAR. October 2014; DOI: 10.1093. In additional numerous transcriptional repressor systems are well known in the art and can be used to turn off gene expression.

VI.B Controlled Proteolysis

In particular, the invention describes the use of controlled protein degradation or proteolysis to provide the control over metabolic fluxes in controlled multi-stage fermentation processes. There are several methodologies known in the art for controlled protein degradation, including but not limited to targeted protein cleavage by a specific protease and controlled targeting of proteins for degradation by specific peptide tags. Systems for the use of the *E. coli* clpXP protease for controlled protein degradation are taught by McGinness et al, "Engineering controllable protein degradation", Mol Cell. June 2006; 22 (5) p701-707. This methodology relies upon adding a specific C-terminal peptide tag such as a DAS4 (or DAS+4) tag. Proteins with this tag are not degraded by the clpXP protease until the specificity enhancing chaperone sspB is expressed. sspB induces degradation of DAS4 tagged proteins by the clpXP protease. In additional numerous site-specific protease systems are well known in the art. Proteins can be engineered to contain a specific target site of a given protease and then cleaved after the controlled expression of the protease. In some aspects, the cleavage can be expected lead to protein inactivation or degradation. For example Schmidt et al ("ClpS is the recognition component for *Escherichia coli* substrates of the N-end rule degradation pathway" Molecular Microbiology March 2009. 72 (2), 506-517. doi: 10.1111), teaches that an N-terminal sequence can be added to a protein of interest in providing clpS dependent clpAP degradation. In addition, this sequence can further be masked by an additional N-terminal sequence, which can be controllable cleaved such as by a ULP hydrolase. This allows for controlled N-rule degradation dependent on hydrolase expression. It is therefore possible to tag proteins for controlled proteolysis either at the N-terminus or C-terminus. The preference of using an N-terminal vs. C-terminal tag will largely depend on whether either tag affects protein function prior to the controlled onset of degradation.

The invention describes the use of controlled protein degradation or proteolysis to provide the control over metabolic fluxes in controlled multi-stage fermentation processes, in *E. coli*. There are several methodologies known in the art for controlled protein degradation in other microbial hosts, including a wide range of gram-negative as well as gram-positive bacteria, yeast and even archaea. In particular, systems for controlled proteolysis can be transferred from a native microbial host and used in a non-native host. For example, Grilly et al, "A synthetic gene network for tuning protein degradation in *Saccharomyces cerevisiae*" Molecular Systems Biology 3, Article 127. doi: 10.1038, teaches the expression and use of the *E. coli* clpXP protease in the yeast *Saccharomyces cerevisiae*. Such approaches can be used to transfer the methodology for synthetic metabolic valves to any genetically tractable host.

VI.C Synthetic Metabolic Valve Control

The invention describes the use of synthetic metabolic valves to control metabolic fluxes in multi-stage fermentation processes. There are numerous methodologies known in the art to induce expression that can be used at the transition between stages in multi-stage fermentations. These include but are not limited to artificial chemical inducers including: tetracycline, anhydrotetracycline, lactose, IPTG (isopropyl-beta-D-1-thiogalactopyranoside), arabinose, raffinose, tryptophan and numerous others. Systems linking the use of these well-known inducers to the control of gene expression silencing and/or controlled proteolysis can be integrated into genetically modified microbial systems to control the transition between growth and production phases in multi-stage fermentation processes.

In addition, it may be desirable to control the transition between growth and production in multi-stage fermentations by the depletion of one or more limiting nutrients that are consumed during growth. Limiting nutrients can include but are not limited to: phosphate, nitrogen, sulfur, and magnesium. Natural gene expression systems that respond to these nutrient limitations can be used to operably link the control of gene expression silencing and/or controlled proteolysis to the transition between growth and production phases in multi-stage fermentation processes.

EXAMPLES

For the purposes of promoting an understanding of the principles of the present disclosure, reference will now be made to preferred aspects and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Methods

Unless otherwise stated, all materials and reagents were of the highest grade possible.

Reagents and Media

LB Broth (Lennox) formulation was used for strain culturing and plasmid propagation and construction. SM10++ and SM10 no phosphate media were prepared as previously reported. Appropriate antibiotics were used in all medias with working concentrations as followed: kanamycin: 35 µg/mL, chloramphenicol: 35 µg/mL, zeocin: 100 µg/mL, blasticidin: 100 µg/mL, gentamicin: 10 µg/mL, ampicillin, 100 ug/mL.

Strains & Plasmids Construction

Sequences of oligonucleotides and synthetic linear DNA (Gblocks™) used in strain construction were obtained from Integrated DNA Technologies (IDT, Coralville, IA). Plasmids, used in this study are presented in the table of FIG. 2. Strains used in this study are presented in the table of FIG. 3. New strains were made using standard recombineering methodologies through the integration of antibiotic resistance cassettes and direct selection. The recombineering plasmid pSIM5 was a gift from Donald Court (NCI, redrecombineering.ncifcrf.gov/court-lab.html). Chromosomal modifications were confirmed by PCR amplification and sequencing (Genewiz/Azenta). pCASCADE silencing plasmids were constructed as previously reported. The stability of guide RNA arrays was confirmed by colony PCR prior to strain evaluations as previously described.

Microfermentations 96 well plate based microfermentations were performed (in triplicate) as detailed previously, by first inoculating 5 ul of frozen glycerol stocks in 145 ul of LB with appropriate antibiotics (kanamycin and chloramphenicol) for 16 hours at 37 degrees with 300 rpm shaking. 5 ul of culture was inoculated in 145 ul of SM10$^{++}$ for 16 hours. Cells were harvested by centrifugation before washing with 150 ul of SM10 no phosphate media. Cells were resuspended in 100 ul of SM10 no phosphate media. 10 ul of each culture was diluted to 200 ul for OD600 reading. Normalization of each well to an OD=1 was done by adding an appropriate volume of the 100 ul culture to a final volume of 150 ul (no phosphate media) in a fresh plate. Plates were incubated for 24 hours at 37 degrees with 300 rpm shaking. After 24 hours, OD600 was taken for each well and the volume was transferred to a U bottom 96 well plate. Cells were pelleted by centrifugation at 3500 g for 10 minutes and the supernatant was isolated for measurement.

Spectrophotometric Measurement of THN/Flaviolin

Relative THN/flaviolin levels were determined using a Spectramax 384-plus plate reader as previously reported. THN/flaviolin production was determined non-quantitatively in 96 flat bottom plates by measuring absorbance at 495 nm divided by the measurement of OD600 of the culture post production. Both measurements were multiplied by appropriate pathlength of volume in 96 well plate and diluted prior to analysis.

Quantification of FabI and GlnB Levels

Quantification of protein levels was performed using strain variants with C-terminal sfGFP tags (see FIG. 2). GFP levels were quantified by ELISA using a quantification kit from AbCam (Cambridge, UK, product #ab171581) according to manufacturer's instructions. Briefly, samples were obtained from microfermentations 24 h post phosphate depletion, washed in water and lysed with the provided extraction buffer.

Example 1: Valve Construction & Validation

We have previously been shown that metabolic valves relying on the combination of silencing and proteolysis (FIG. 1) resulted in a >95% reduction in Zwf levels and an 80% reduction in GltA levels. Our previous studies did not include validation of dynamic control over GlnB levels or the successful use of proteolysis in combination with silencing to reduce FabI levels. We previously demonstrated that leaky expression of a gRNA silencing fabI, led to a growth defect and gRNA instability, requiring reconstruction of a host strain enabling tighter control over the silencing machinery. As a result, in our prior work, dynamic control over FabI levels relied on proteolysis alone. In this study, we first used these more stable host strains to evaluate the combination of silencing and proteolysis on FabI as well as GlnB levels. To do this we leveraged strains incorporating a C-terminal sfGFP tag with and without a degron tag behind fabI or glnB (FIG. 2). These tags enable absolute quantification of protein levels using an ELISA to measure GFP. Results of these studies are given in FIG. 4. In the case of GlnB we evaluated gRNAs silencing the two promoters driving glnB expression, alone and in combination. The combination of proteolysis and silencing led to a 99% and 95% reduction in FabI and GlnB levels, respectively. For GlnB, the combination of proteolysis with silencing of the glnBp2 promoter had the largest reduction in protein levels. As a result, this silencing gRNA was used in subsequent strain combinations.

Example 2: Measuring Relative Malonyl-CoA Flux in vivo

To rapidly quantify improvements in malonyl-CoA fluxes we leveraged a single enzyme (THNS synthase, encoded by the rppA gene from S. griseolis) capable of producing 1 mole of 1,3,6,8-tetrahydroxynaphthalene (THN) from 5 moles of malonyl-CoA. The use of 1,3,6,8-tetrahydroxynaphthalene (THN) as "malonyl-CoA reporter" have been well established. Relative THN levels can be quantified by absorbance at 495 nm, and additionally THN spontaneously oxidizes to the purple-colored product flaviolin. Specifically, we cloned and expressed rppA behind the tightly controlled robust low phosphate inducible yibD gene promoter.

Figure 5:
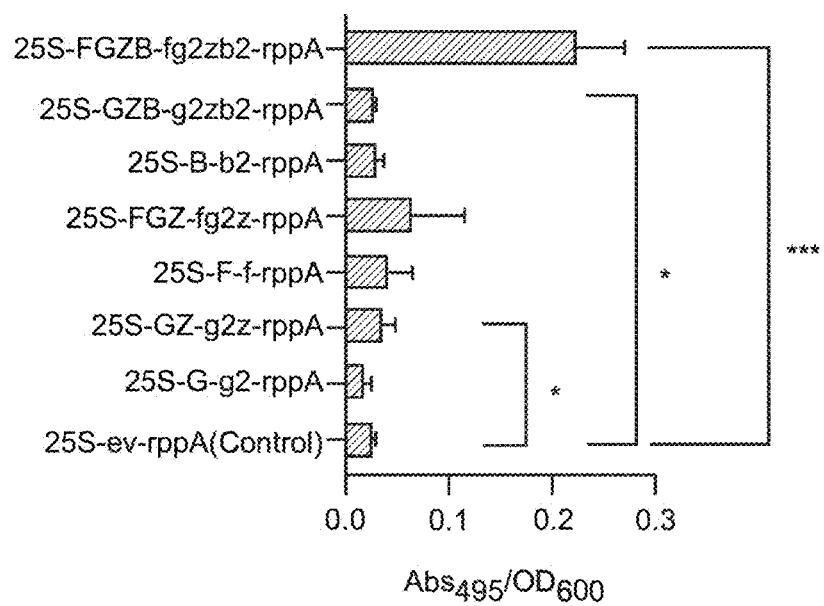
FIG. 5 is a graph representing impact of dynamic control over GltA, Zwf, FabI, GlnB levels on THN/Flaviolin production in minimal media microfermentations. Strains contain both proteolytic and transcription valves as described in FIG. 1B. All strains were done in triplicate and normalized to OD=1 prior to production in phosphate free media. Two sample t tests were conducted comparing engineered strains to control. * indicates p value

Using this construct, we evaluated the impact of dynamic control of our "valves" on the two-stage production of THN. Specifically, strains tested included a set of "G" (citrate synthase), "Z" (glucose 6-phosphate dehydrogenase), "F" (enoyl-ACP reductase), and "B" (nitrogen regulator protein P-II) valves (FIG. 1). Refer to Table 1 for a list of plasmids and strains used in this study. As hypothesized the "G" valve led to reduction in THN production compared to the no-valve control, presumably due to reduced alpha-ketoglutarate levels and GlnB mediated ACCase inhibition. The "B" valve alone had no impact on THN synthesis. The addition of the "Z" valve ("G", "Z" strain) improved THN production to 149% of the control. As acetyl-CoA is a known activator of ACCase, as well as substrate, improved acetyl-CoA levels are expected to improve malonyl-CoA flux. The best producing strain had all valve combinations ("G", "Z", "F" and "B") (FIG. 5). There was a 916% improvement when all valves were present, highlighting a synergistic effects of the valves compared to either valve alone (G, B, F). The combination of "G" "Z" with "B" did not improve production compared to the "GZ" strain. This was somewhat unexpected in light of the final four valve combination. We hypothesize that in the "GZ" background, acyl-ACP levels are the primary regulator of malonyl-CoA flux and that GlnB based inhibition becomes limiting only after reductions in acyl-ACP pools due to the "F" valve. The "Z" valve, alone, was not tested given its relatively lower improvement to enhance flux to acetyl-coA in previous work.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

The invention claimed is:

1. A genetically modified microorganism comprising:
   a first synthetic metabolic valve for dynamic and selective regulation of a nitrogen regulatory protein (glnB), the synthetic metabolic valve comprising:
   gene expression-silencing of a glnB gene,
   selective enzymatic degradation of a glnB protein, or
   a combination thereof,
   wherein the synthetic metabolic valve is selectively activated to silence a glnB gene and/or degrade a glnB protein in response to depletion of phosphate as a limiting nutrient in the growth media in which the genetically modified microorganism is growing.

2. The genetically modified microorganism of claim 1 further comprising:
   at least one additional synthetic metabolic valve(s) comprising:
   a gene expression-silencing synthetic metabolic valve silencing gene expression of one or more genes in addition to the glnB gene; or
   a selective enzymatic degradation synthetic metabolic valve inducing selective enzymatic degradation of one or more proteins in addition to the glnB protein, or
   a combination thereof.

3. The genetically modified microorganism of claim 2, wherein the additional synthetic metabolic valves are directed to silencing a gene that is: enoyl-ACP reductase (fabI), citrate synthase (gltA), glucose-6-phosphate-1-dehydrogenase (zwf), or combinations thereof;
   Response to final Office action dated Dec. 27, 2024 or the additional synthetic metabolic valves are directed to selective enzymatic degradation of a protein that is: enoyl-ACP reductase (fabI), citrate synthase (gltA), glucose-6-phosphate-1-dehydrogenase (zwf), or combinations thereof.

4. The genetically modified microorganism of claim 1 further comprising:
   a second synthetic metabolic valve for dynamic and selective regulation of enoyl-ACP reductase (fabI), the synthetic metabolic valve comprising:
   gene expression-silencing of a fabI gene,
   selective enzymatic degradation of fabI protein, or
   a combination thereof; and
   a third synthetic metabolic valve for dynamic and selective regulation of glucose-6-phosphate-1-dehydrogenase (zwf), the synthetic metabolic valve comprising:
   gene expression-silencing of a zwf gene,
   selective enzymatic degradation of zwf protein, or
   a combination thereof; and
   a fourth synthetic metabolic valve for dynamic and selective regulation of citrate synthase (gltA), the synthetic metabolic valve comprising:
   gene expression-silencing of a gltA gene,
   selective enzymatic degradation of gltA protein, or
   a combination thereof.

5. The genetically modified microorganism of claim 1, wherein the genetically modified microorganism is an *E. coli* microorganism.

6. The genetically modified microorganism of claim 2, wherein the synthetic metabolic valve comprises:
   a gene encoding at least one small guide RNA specific for targeting more than one gene of an enzyme essential for growth of the genetically modified microorganism.

7. A bioprocess for production of a product from a genetically modified microorganism, the bioprocess comprising:
   (a) providing a genetically modified microorganism comprising:
      (i) a production pathway for a product, the production pathway having malonyl-CoA as a biosynthetic precursor of the product;
      (ii) a synthetic metabolic valve for dynamic and selective regulation of a nitrogen regulatory protein (glnB), the synthetic metabolic valve comprising:
      gene expression-silencing of a glnB gene,
      selective enzymatic degradation of a glnB protein, or
      a combination thereof; and
      (iii) an additional synthetic metabolic valve(s) for dynamic and selective regulation of one or more genes in addition to the glnB gene; or
   a selective enzymatic degradation of one or more proteins in addition to the glnB protein;
   (b) growing the genetically modified microorganism in a media;
   (c) transitioning from microorganism growth to stationary productive phase, the transition comprising:
      (i) reducing or stopping genetically modified microorganism growth at least partially by controlled depletion of phosphate as a limiting nutrient from the media
      (ii) activation of synthetic metabolic valves
      (iii) increasing the available malonyl-CoA pool;

(d) producing a product in the stationary productive phase.

8. The bioprocess of claim 7, wherein the genetically modified microorganism is an *E. coli* microorganism.

9. The bioprocess of claim 7, wherein the additional synthetic metabolic valves are directed to silencing a gene that is: enoyl-ACP reductase (fabI), citrate synthase (gltA), glucose-6-phosphate-1-dehydrogenase (zwf), or combinations thereof; or the additional synthetic metabolic valves are directed to selective enzymatic degradation of a protein that is: enoyl-ACP reductase (fabI), citrate synthase (gltA), glucose-6-phosphate-1-dehydrogenase (zwf), or combinations thereof.

* * * * *